May 14, 1957 W. F. CONNELL Plant Pat. 1,602
APPLE TREE
Filed June 28, 1955
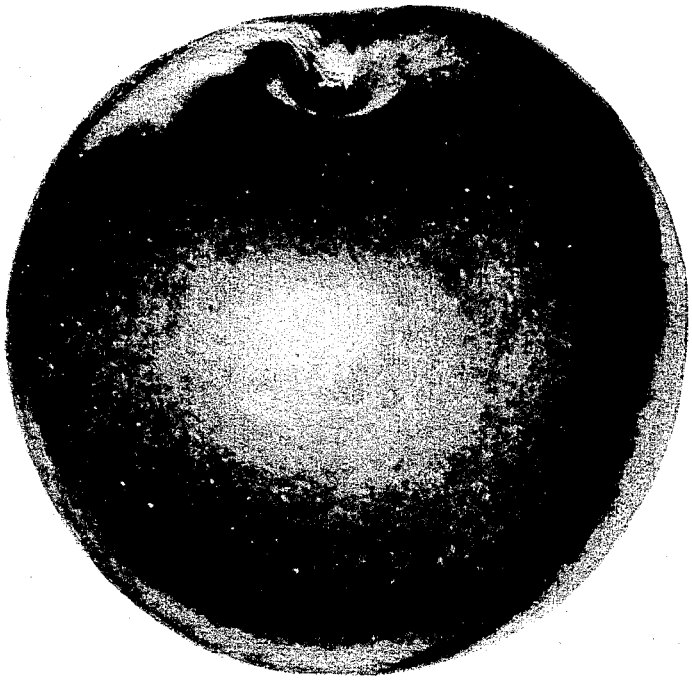

United States Patent Office

Plant Pat. 1,602
Patented May 14, 1957

1,602

APPLE TREE

William F. Connell, Menomonie, Wis.

Application June 28, 1955, Serial No. 518,692

1 Claim. (Cl. 47—62)

This discovery is a bud sport of the Fireside variety of apple tree and was originally grown by me on my farm at Menomonie, Wisconsin. The Fireside variety was originally developed at the University of Minnesota Fruit Breeding Farm at Excelsior, Minnesota and, while the same has not been patented, a description thereof has been filed with the United States Department of Agriculture and the University of California Register of Fruit and Nut Varieties, located at Davis, California.

I have asexually reproduced this new variety at Menomonie, Wisconsin by top grafting a branch from the original sport to a growing tree and have carefully observed the same and tested the variety over a period of time to determine its permanent characteristics and desirability for commercial purposes.

This new bud sport is very similar in its characteristics to the Fireside variety. However, its substantially uniform dark red color clearly distinguishes the fruit from the Fireside variety since the principal undesirable characteristic of the Fireside fruit was the generally light background color thereof. This new variety has the same rich sweet fruit flavor and firm crisp fruit quality with excellent storage characteristics as is present in the Fireside variety, as well as the relatively large, substantially round symmetrical shape of the Fireside variety.

The following is a detailed description of the new variety made with reference to specimens of the plant grown on my above identified farm.

In the accompanying drawing there is illustrated a specimen of the new apple depicting the uniform dark red color.

This apple matures late in the season with its first maturity for eating approximately September 20 and the date for last picking approximately October 15, depending, of course, upon the weather conditions.

Tree: Similar to the Fireside. Medium; vigorous; spreading; medium density; round topped; medium growing; very hardy; regular bearing.

Trunk: Similar to the Fireside. Stocky; smooth; brownish in color.

Branches: Similar to the Fireside. Medium in number; brown to reddish-brown in color; extremely strong with well formed strong crutches.

Leaves: Similar to the Fireside.

Fruit: Matures for eating by September 20. Similar to the Fireside.

*Size.*—Uniform and large. Diameter—approximately 3 inches. Similar to the Fireside.

*Form.*—Rounded; slightly conic. Similar to the Fireside.

*Cavity.*—Symmetrical; flaring slightly less than 1 inch in depth. Breadth—slightly less than ½ inch, with outer portion thereof being slightly russet in color and the inner portion being yellowish-green in color.

*Basin.* — Generally symmetrical; well-formed. Depth—slightly less than ¾ inch. Breadth— approximately 1¼ inches. Similar to the Fireside.

Stem: Strong and clings tenaciously to tree; very resistant to wind; slender; approximately ¾ inch in length; little if any extrusion beyond the cavity; having slight pubescence and slightly roughened outer surface. Similar to the Fireside.

Calyx: Closed, with a conic calyx tube; segments slightly pubescent on the inner and outer surfaces and converging outwardly from the base to the center.

Skin: Thin; generally smooth; glossy; waxed.

*Dots.*—Fairly conspicuous; slightly protruding; medium in number.

*Color of dots.*—Creamy yellow.

*Description of dots.*—Generally evenly distributed but being slightly more numerous toward the upper portion of the fruit.

*Color.*—Extremely attractive dark red color; slightly darker than Chrysanthemum Crimson No. 824 and slightly lighter than Indian Lake No. 826 (Horticultural Colour Chart, issued by The British Colour Council in collaboration with The Royal Horticultural Society). This new variety has a much more attractive color than the Fireside and, instead of having the numerous light red stripes over a bright greenish-yellow ground, has a generally uniform, dark red color over its entire area.

Bloom: Scant.

Flesh: Generally similar to the Fireside. Juicy; creamy white.

*Texture.*—Firm; tender; crisp.

*Flavor.*—Rich; sweet; non-tart; very mildly acid.

*Aroma.*—Slight.

*Quality.*—Excellent.

Core: Generally similar to the Fireside. Medium position; generally small.

*Bundle area.*—Medium size; oblate; symmetrical.

*Halves of area.*—Equal.

*Bundles.*—Greenish-yellow; inconspicuous.

*Core lines.*—Distinct at outer middle portions, becoming indistinct at the upper and lower ends.

*Seed cells.*—Closed.

*Cell walls.*—Thin. Length—¾ inch; breadth—½ inch.

Seeds:

*Number perfect.*—Numerous (8 to 14).

*Number in one cell.*—2 to 4. Length—⅜ inch. Breadth—slightly over ⅛ inch.

*Form.*—Obtuse.

*Color.*—Medium brown.

Use: Dessert; excellent eating quality; excellent cooking quality; excellent marketing and shipping quality. Similar to the Fireside.

Keeping quality: Excellent under commercial storage conditions; maintains uniform excellent quality from November through April. Generally similar to the Fireside.

Resistance to diseases: Highly resistant to cedar rust but has medium resistance to apple scab and fire blight. Generally similar to Fireside. My trees are now being grown in Wisconsin, Minnesota, Iowa and Oregon and have exhibited the above characteristic resistance to diseases.

I claim:

A new and distinct variety of apple tree characterized as to novelty by the attractive uniform dark red color, rich sweet flavor of its fruit, and its excellent shipping and storage quality.

No references cited.